United States Patent [19]

Takamine et al.

[11] Patent Number: 5,442,114
[45] Date of Patent: Aug. 15, 1995

[54] PROCESS FOR PRODUCING AROMATIC AMIDE COMPOUNDS

[75] Inventors: Kan Takamine; Michio Yamato; Akira Murakami; Tooru Tokumaru, all of Oita; Yoshinori Nakayama, Ibaraki; Motoo Hazama, Oita, all of Japan

[73] Assignee: Sumitomo Chemical Company, Limited, Osaka, Japan

[21] Appl. No.: 182,460

[22] Filed: Jan. 18, 1994

[30] Foreign Application Priority Data

| Jan. 29, 1993 | [JP] | Japan | 5-013646 |
| Jan. 29, 1993 | [JP] | Japan | 5-013647 |
| Oct. 6, 1993 | [JP] | Japan | 5-250598 |
| Oct. 6, 1993 | [JP] | Japan | 5-250599 |

[51] Int. Cl.$^6$ .......................... C07C 231/02
[52] U.S. Cl. .................. 564/142; 564/397; 564/398; 564/416; 564/417; 564/418; 564/420; 564/421; 564/422; 564/423
[58] Field of Search ............... 564/142, 397, 398, 416, 564/417, 418, 420, 421, 422, 423; 430/543, 546, 553

[56] References Cited

U.S. PATENT DOCUMENTS

| 2,801,171 | 7/1957 | Fierke et al. | 430/546 |
| 3,772,002 | 11/1973 | Ramello | 430/553 |
| 4,126,461 | 11/1978 | Pupo et al. | 96/50 |
| 4,500,635 | 2/1985 | Aoki et al. | 430/552 |
| 4,686,177 | 8/1987 | Aoki et al. | 430/553 |
| 4,990,671 | 2/1991 | Dunski et al. | 564/418 |

FOREIGN PATENT DOCUMENTS

| 0121365 | 10/1984 | European Pat. Off. |  |
| WO010347 | 11/1989 | European Pat. Off. |  |
| 347283 | 12/1989 | European Pat. Off. | 564/417 |
| 490218 | 6/1992 | European Pat. Off. | 564/417 |
| 2394832 | 6/1978 | France. |  |
| 3527116 | 2/1986 | Germany. |  |
| 60-209735 | 10/1985 | Japan. |  |
| 3110553 | 5/1991 | Japan | 564/142 |
| 4046141 | 2/1992 | Japan | 564/417 |
| 532598 | 2/1993 | Japan. |  |
| 1680690 | 9/1991 | U.S.S.R. | 564/417 |

Primary Examiner—Shailendra Kumar
Attorney, Agent, or Firm—Birch, Stewart, Kolasch & Birch

[57] ABSTRACT

There is disclosed a process for producing an aromatic amide compound of the general formula (4), including the steps of subjecting an o-nitrophenol compound of the general formula (1) to catalytic reduction in acetone or an aromatic hydrocarbon solvent under the presence of a nickel catalyst to give an o-aminophenol compound of the general formula (2); and (b) subjecting the o-aminophenol compound of the general formula (2) to condensation with an acid chloride compound having a sulfur content of 0.5% or less, based on the weight of the acid chloride compound, of the general formula (3) in acetone or an aromatic hydrocarbon solvent under an atmosphere of an inert gas having an oxygen concentration of 1% or less. The acid chloride compound having a sulfur content of 0.5% or less, based on the weight of the acid chloride compound, of the general formula (3) may be obtained by allowing a carboxylic acid compound of the general formula (5) to react with thionyl chloride and by concentrating the reaction mixture. Also disclosed is another process for producing an aromatic amide compound of the general formula (4), including the step of subjecting an o-aminophenol hydrochloride salt of the general formula (6) to condensation with an acid chloride compound having a sulfur content of 0.8% or less, based on the weight of the acid chloride compound, of the general formula (3) in an inert solvent.

14 Claims, No Drawings

PROCESS FOR PRODUCING AROMATIC AMIDE COMPOUNDS

FIELD OF THE INVENTION

The present invention relates to a process for producing aromatic amide compounds that are used as a cyan coupler for color photographs.

BACKGROUND OF THE INVENTION

As the process for producing aromatic amide compounds that are used as a cyan coupler for color photographs, there have hitherto been known a process in which o-nitrophenol compounds are reduced in methanol to give o-aminophenol compounds and after removal of the solvent, the resultant o-aminophenol compounds are subjected to condensation with acid chloride compounds in acetic acid under the presence of sodium acetate (see, e.g., JP-A 62-73258); and a process in which o-aminophenol hydrochloride salts are allowed to react with acid chloride compounds in acetone under the presence of quinoline to give the aromatic amide compound in a yield of 37% (see, e.g., U.S. Pat. No. 2,801,171).

However, these process have the following disadvantages: the former process requires complicated operations, e.g., solvent replacement with an acidic solvent such as acetic acid in the condensation reaction through amidation (hereinafter referred to as amidation condensation), and the latter process requires less available reagents such as quinoline. Further, these processes cannot provide aromatic amide compounds in a satisfactory yield.

SUMMARY OF THE INVENTION

Under these circumstances, the present inventors have intensively studied to develop a process for producing a high-quality cyan coupler for color photographs in a high yield on an industrial scale. As the result, they have found that an aromatic amide compound can be obtained in a high yield by the amidation condensation of an o-aminophenol compound with an acid chloride compound having a sulfur content of 0.5% or less, based on the weight of the acid chloride compound, under an atmosphere of an inert gas having an oxygen concentration of 1% or less without any solvent replacement, wherein the o-aminophenol compound is obtained by the reduction of an o-nitrophenol compound in acetone or an aromatic hydrocarbon solvent under the presence of a nickel catalyst. They have also found that an aromatic amide compound can be obtained in a high yield by the amidation condensation of an o-aminophenol hydrochloride salt with an acid chloride compound having a sulfur content of 0.8% or less, based on the weight of the acid chloride compound, in an inert solvent with no use of reagents such as acetic acid or quinoline, thereby completing the present invention.

Thus, the present invention provides a process for producing an aromatic amide compound of the general formula:

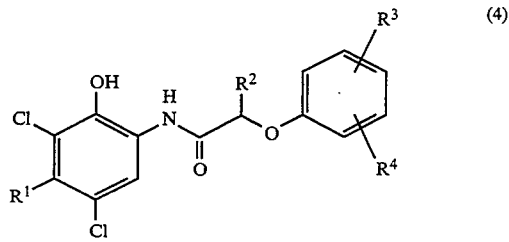

wherein $R^1$ is a $C_1$–$C_4$ alkyl group, and $R^2$, $R^3$ and $R^4$ are independently a hydrogen atom or a $C_1$–$C_6$ alkyl gruop, which process is characterized in that:

(a) an o-nitrophenol compound of the general formula:

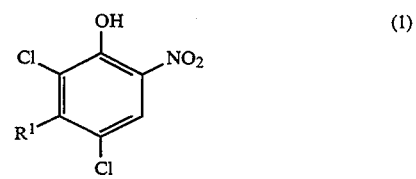

wherein $R^1$ is as defined above, is subjected to catalytic reduction in acetone or an aromatic hydrocarbon solvent under the presence of a nickel catalyst to give an o-aminophenol compound of the general formula:

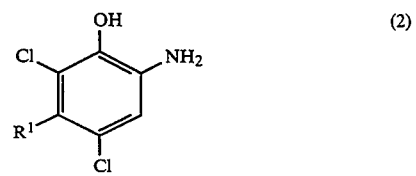

wherein $R^1$ is as defined above; and (b) the o-aminophenol compound obtained in the step (a) is then subjected to condensation with an acid chloride compound having a sulfur content of 0.5% or less, based on the weight of the acid chloride compound, of the general formula:

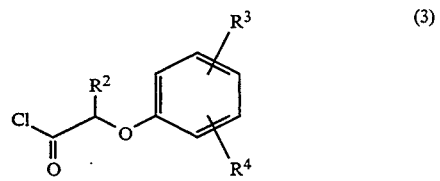

wherein $R^2$, $R^3$ and $R^4$ are each as defined above, in acetone or an aromatic hydrocarbon solvent under an atmosphere of an inert gas having an oxygen concentration of 1% or less. The acid chloride compound having a sulfur content of 0.5% or less, based on the weight of the acid chloride compound, of the general formula (3) may be obtained by the reaction of a carboxylic acid compound of the general formula:

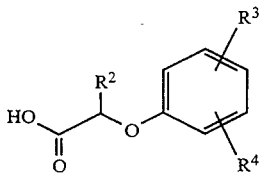

wherein $R^2$, $R^3$ and $R^4$ are each as defined above, with thionyl chloride and by the concentration of the resultant reaction mixture.

The present invention also provides another process for producing an aromatic amide compound of the general formula:

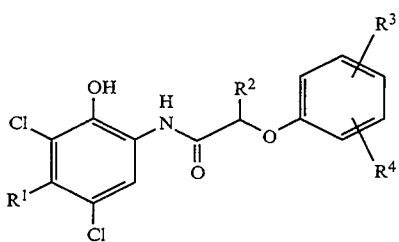

wherein $R^1$, $R^2$, $R^3$ and $R^4$ are each as defined above, which process is characterized in that:

(a) an o-aminophenol hydrochloride salt of the general formula:

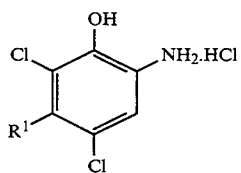

wherein $R^1$ is as defined above, is subjected to condensation with an acid chloride compound having a sulfur content of 0.8% or less, based on the weight of the acid chloride compound, of the general formula:

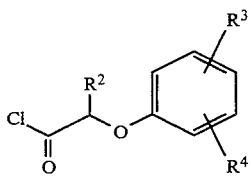

wherein $R^2$, $R^3$ and $R^4$ are each as defined above, in an inert solvent.

DETAILED DESCRIPTION OF THE INVENTION

The following will describe the first step in the first production process of the present invention, that is, the step (a) of subjecting an o-nitrophenol compound of the general formula (1) to catalytic reduction in acetone or an aromatic hydrocarbon solvent under the presence of a nickel catalyst to give an o-aminophenol compound of the general formula (2).

The starting material to be used in the catalytic reduction is an o-nitrophenol compound of the general formula (1), wherein $R^1$ is a $C_1$–$C_4$ alkyl group such as a methyl, an ethyl, a n-propyl, an isopropyl, a n-butyl or a sec-butyl group. These kinds of the o-nitrophenol compound can readily be obtained by any one of the methods described in JP-A 47-34326, JP-A 61-57536, JP-A 61-60634, JP-A 64-47741 and JP-A 63-303958.

Typical examples of the o-nitrophenol compound are 2-nitro-4,6-dichloro-5-methylphenol, 2-nitro-4,6-dichloro-5-ethylphenol, 2-nitro-4,6-dichloro-5-n-propylphenol, 2-nitro-4,6-dichloro-5-isopropylphenol, 2-nitro-4,6-dichloro-5-n-butylphenol and 2-nitro-4,6-dichloro-5-sec-butylphenol.

The o-nitrophenol compound of the general formula (1) is subjected to catalytic reduction in acetone or an aromatic hydrocarbon solvent such as toluene or xylene. The amount of solvent to be used is usually 1 to 10 times, preferably 2 to 6 times, as much as the weight of the raw material o-nitrophenol compound. These solvents can be used without any solvent replacement even in the subsequent amidation condensation step, and therefore, only one solvent may be used in all the steps including the hydrogenation step. In this regard, the production process of the present invention is quite advantageous from an industrial point of view, because the solvent can readily be recycled for its repeated use.

The catalyst to be used in the catalytic reduction is a nickel catalyst. Typical examples of the nickel catalyst are Raney nickel or catalysts carrying nickel on a support such as activated carbon or a metal oxide (e.g., alumina, magnesia, silica, titania, zirconia). The amount of catalyst is dependent upon the content of nickel. The amount of nickel used for the reaction is usually 0.1% to 6% by weight, preferably 0.5% to 3% by weight, based on the weight of the raw material o-nitrophenol compound.

The use of a nickel catalyst makes it possible to reduce the amount of monochlorinated impurities produced by the replacement of a chlorine atom in the chlorinated o-aminophenol compound with a hydrogen atom. Hence the reaction selectivity to the o-aminophenol compound of the general formula (2), which is a target compound for the reduction, is improved. To increase the reaction selectivity, the reduction is preferably carried out under the coexistence of activated carbon. The reduction may be carried out under ordinary pressure or increased pressure, usually under a hydrogen pressure of 0.1 to 20 kg/cm² (gauge pressure), at a temperature of 20° to 60° C., preferably 30° to 50° C.

After completion of the reaction, the reaction mixture containing the o-aminophenol compound obtained by the reduction can be subjected to the subsequent condensation with an acid chloride compound of the general formula (3) without any further treatment or after removal of the reduction catalyst by filtration; if necessary, the condensation may be carried out after adjustment of the solvent amount. The o-aminophenol compound thus obtained is kept under an atmosphere of an inert gas having an oxygen concentration of 1% or less, because the o-aminophenol is liable to form colored ingredients in air, which finally deteriorate the quality of the armatic amide compound. Under this condition, the o-aminophenol compound can be stored for about 30 hours without being deteriorated, so that them is no problem in the yield and quality of an aromatic amide compound obtained by the amidation condensation of this o-aminophenol compound.

The o-aminophenol compound obtained in this manner can be used, as described below, without any solvent replacement which is done in a conventional process. In this regard, the production process of the present invention is quite advantageous, because complicated operations are not required.

In the o-aminophenol compound of the general formula (2) obtained by the above reaction, the substituent $R^1$ is a $C_1$–$C_4$ alkyl group such as a methyl, an ethyl, a n-propyl, an isopropyl, a n-butyl or a sec-butyl group.

Typical examples of the o-aminophenol compound are 2-amino-4,6-dichloro-5-methylphenol, 2-amino-4,6-dichloro-5-ethylphenol, 2-amino-4,6-dichloro-5-n-propylphenyl, 2-amino-4,6-dichloro-5-isopropylphenol, 2-amino-4,6-dichloro-5-n-butylphenol and 2-amino-4,6-dichloro-5-sec-butylphenol.

The following will describe the acid chloride compound of the general formula (3), which is the other starting material to be used in the amidation condensation.

In this amidation condensation, if the remaining sulfur content, based on the weight of the acid chloride compound, is more than 0.5%, the yield of the aromatic amide compound obtained is remarkably reduced, as shown in the comparative examples below. For this reason, an acid chloride compound of the general formula (3) having a sulfur content of 0.5% or less, based on the weight of the acid chloride compound, is used.

Such an acid chloride compound can also be produced using a reagent having no sulfur content, such as phosgene or oxalyl chloride, other than thionyl chloride.

The acid chloride compound of the general formula (3) having a sulfur content of 0.5% or less is obtained by distillating a crude acid chloride compound which is obtained by a reaction of a carboxylic acid compound (5) with thionyl chloride.

More preferred is an acid chloride compound of the general formula (3), which is obtained without any distillation as described above, for example, by the reaction of a carboxylic acid compound of the general formula:

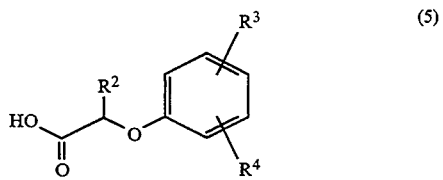

wherein $R^2$, $R^3$ and $R^4$ are independently a hydrogen atom or a $C_1$–$C_6$ alkyl group, with thionyl chloride, the reaction mixture of which is then concentrated to have a sulfur content of 0.5% or less.

Thus, in the first production process of the present invention, an acid chloride compound to be reacted with an o-aminophenol compound for the amidation condensation can readily be obtained in a high yield by the concentration of a reaction mixture obtained after the reaction of a carboxylic acid compound with thionyl chloride, for the adjustment of its sulfur content without any distillation of the acid chloride compound.

The concentration of a solution containing the acid chloride compound is carried out, for example, at 65° C. under a reduced pressure of 30 mmHg, or when a reaction solvent is used in the reaction for obtaining the acid chloride compound, the amount of reaction solvent remaining after the concentration is usually reduced to 50% by weight or less, preferably 20% by weight or less, as compared with the amount of reaction solvent before the concentration.

In the reaction for obtaining an acid chloride compound from a carboxylic acid compound using thionyl chloride, the amount of thionyl chloride to be used is usually 1 to 6 times, preferably 1 to 2 times, as much as the mole of the carboxylic acid compound. The reaction is usually carried out at a temperature of 40° to 80° C. under a stream of an inert gas such as nitrogen gas, optionally with the addition of a pyridine compound, such as pyridine or picoline, or an amide compound, such as N,N-dimethylformamide or N-methylpyrrolidone, in an amount of 5% by mole or less, to the raw material carboxylic acid compound.

Examples of the reaction solvent are aromatic hydrocarbons such as toluene and xylene. These solvents are usually used in an amount of 0.1 to 5 times as much as the weight of the carboxylic acid compound. It is not always essential to use such a reaction solvent.

With the use of an acid chloride compound obtained in such a manner, the yields of an aromatic amide compound, not only from the o-nitrophenol compound which is one of the raw materials, but also from the carboxylic acid compound which is the other raw material, are improved.

In the acid chloride compound of the general formula (2), the substituents $R^2$, $R^3$ and $R^4$ are independently a hydrogen atom or a $C_1$–$C_6$ alkyl group such as a methyl, an ethyl, a n-propyl, an isopropyl, a n-butyl, an isobutyl, a sec-butyl, a tobutyl, a n-amyl, an isoamyl, a sec-amyl, a t-amyl, a neo-pentyl, a n-hexyl, a 2-hexyl, a 3-hexyl or a t-hexyl group.

Typical examples of the acid chloride compound are (2-ethylphenoxy)acetyl chloride, (4-ethylphenoxy)acetyl chloride, 2-(2-isopropylphenoxy)butyryl chloride, 2-(3,5-diisopropylphenoxy)butyryl chloride, 2-(2-t-amyl-4-methylphenoxy)butyryl chloride, 2-(2,4-di-t-amylphenoxy)butyryl chloride, 2-(2,4-di-t-amylphenoxy)valeryl chloride, 2-(2,4-di-t-amylphenoxy)hexanolyl chloride, 2-(2,4-di-t-amylphenoxy)heptanoyl chloride and 2-(2,4-di-t-amylphenoxy)octanoyl chloride.

The following will describe the amidation condensation which is the second step in the first production process of the present invention.

The amount of acid chloride compound to be used is usually in the range of 1 to 1.5 times, preferably 1 to 1.35 times, as much as the mole of the o-aminophenol compound.

Examples of the reaction solvent are acetone and aromatic hydrocarbons such as toluene and xylene. The amount of reaction solvent to be used is usually in the range of 3 to 25 times, preferably 3 to 18 times, as much as the weight of the o-aminophenol compound. The reaction is usually carried out at a temperature of 40° to 100° C. in such a manner that the acid chloride compound is added dropwise to a solution of the o-aminophenol compound.

The amidation condensation is carried out under an atmosphere of an inert gas having an oxygen concentration of 1% or less, for example, under an atmosphere of nitrogen gas, to prevent the deterioration of the o-aminophenol compound by oxygen in the atmosphere.

In this reaction, although hydrogen chloride is generated, it is not necessary to use an acid scavenger, and the reaction can proceed smoothly, even if only both reagents are used. When an acid scavenger is used, the reaction can be carried out more easily, and the amount of solvent to be used can be reduced to 3 to 10 times as much as the weight of the o-aminophenol compound.

Examples of the acid scavenger which can be used are organic bases such as tertiary alkylamines (e.g., triethylamine, tributylamine) and pyridine compounds (e.g., pyridine, picoline); and inorganic bases such as alkali metal carbonates (e.g., sodium carbonate) and alkali metal hydrogencarbonates (e.g., sodium hydrogencarbonate, potassium hydrogencarbonate).

The amount of acid scavenger to be used is usually up to about 1 time as much as the mole of the o-aminophenol compound when a diacidic base is used as the acid scavenger, and it is up to about 2 times as much as the mole of the o-aminophenol compound when a monoacidic base is used as the acid scavenger.

The reaction mixture after the condensation may be subjected to the subsequent crystallization step without any further treatment. When an acid scavenger is used, the reaction mixture is subjected, if necessary, to washing and separation with a separatory funnel, or if necessary, to filtration, after which the reaction mixture is usually subjected to the subsequent crystallization step, although the desired compound can be obtained from the reaction mixture by concentration.

For the subsequent crystallization step, the amount of solvent and the solvent composition are conveniently adjusted by the distillation or addition of the reaction solvent, or if necessary, by the addition of water.

The amount of solvent to be used in the crystallization step is usually in the range of 3 to 15 times as much as the weight of the o-aminophenol compound. To crystallize the product, the solvent composition is adjusted to 10–40% water-containing acetone by adding water to the reaction mixture after amidation condensation. When an aromatic hydrocarbon solvent such as toluene or xylene is used in the amidation condensation step, crystallization can be conducted only by adjusting the amount of solvent.

The crystallization is carried out, while the reaction mixture is usually cooled from a temperature of 40° to 100° C. to a temperature of 5° to 10° C.

The deposited crystals are filtered, washed and dried, which afforded the desired compound as a product having no remaining solvent or water content.

Typical examples of the compound which can be obtained in this production process are 2-(2,4-di-t-amylphenoxy)-N-(3,5-dichloro-4-ethyl-2-hydroxyphenyl)-butyramide, 2-(2,4-di-t-amylphenoxy)-N-(3,5-dichloro-4-methyl-2-hydroxyphenyl)butyramide, 2-(2,4-di-t-amylphenoxy)-N-(3,5-dichloro-4-ethyl-2-hydroxyphenyl)acetamide, 2-(2,4-di-t-amylphenoxy)-N-(3,5-dichloro-4-methyl-2-hydroxyphenyl)acetamide, 2-(2-t-amyl-4-methylphenoxy)-N-(3,5-dichloro-4-ethyl-2-hydroxyphenyl)butyramide, 2-(2-t-amyl-4-methylphenoxy)-N-(3,5-dichloro-4-methyl-2-hydroxyphenyl)butyramide, 2-(2-t-amyl-4-methylphenoxy)-N-(3,5-dichloro-4-ethyl-2-hydroxyphenyl)acetamide, 2-(2-t-amyl-4-methylphenoxy)-N-(3,5-dichloro-4-methyl-2-hydroxyphenyl)acetamide, 2-(2,4-di-t-amylphenoxy)-N-(3,5-dichloro-4-ethyl-2-hydroxyphenyl)valeramide, 2-(2,4-di-t-amylphenoxy)-N-(3,5-dichloro-4-methyl-2-hydroxyphenyl)valeramide, 2-(2,4-di-t-amylphenoxy)-N-(3,5-dichloro-4-methyl-2-hydroxyphenyl)hexanamide, 2-(2,4-di-t-amylphenoxy)-N-(3,5-dichloro-4-methyl-2-hydroxyphenyl)heptanamide and 2-(2,4-di-t-amylphenoxy)-N-(3,5-dichloro-4-methyl-2-hydroxyphenyl)octanamide.

The following will describe a process for the reaction of an o-aminophenol hydrochloride salt of the general formula (6) with an acid chloride compound of the general formula (3), which is the second production process of the present invention.

First, o-aminophenol hydrochloride salts of the general formula (6) to be used in this process will hereinafter be explained.

In the o-aminophenol hydrochloride salt of the general formula (6), the substituent $R^1$ is a $C_1$–$C_4$ alkyl group such as a methyl, an ethyl, a n-propyl, an isopropyl, a n-butyl or a sec-butyl group.

Typical compounds of the o-aminophenol hydrochloride salt are 2-amino-4,6-dichloro-5-methylphenol hydrochloride, 2-amino-4,6-dichloro-5-ethylphenol hydrochloride, 2-amino-4,6-dichloro-5-n-propylphenol hydrochloride, 2-amino-4,6-dichloro-5-isopropylphenol hydrochloride, 2-amino-4,6-dichloro-5-n-butylphenol hydrochloride and 2-amino-4,6-dichloro-5-sec-butylphenol hydrochloride.

These compounds can be obtained by the conversion of o-aminophenol compounds, which are obtained by the reduction of the corresponding nitro compounds, into hydrochloride salts according to conventional procedures.

Next, acid chloride compounds of the general formula (3) will hereinafter be explained.

Examples of the acid chloride compound are similar to those used in the first production process of the present invention. In the second production process of the present invention, the maximum permissible sulfur content of an acid chloride compound is greater than the case of amidation in the first production process of the present invention. Even if an acid chloride compound has a sulfur content of 0.8% or less, based on the weight of the acid chloride compound, it can be used. More preferred is an acid chloride compound of the general formula (3) having a sulfur content of 0.5% or less.

Such an acid chloride compound can also be obtained, for example, by a process in which phosgene or oxalyl chloride having no sulfur content is allowed to react with a carboxylic acid compound.

As the acid chloride compound of the general formula (3), those having a sulfur content of 0.8% or less, preferably 0.5% or less, may be used, which can be obtained by distillating a crude acid chloride compoud which is obtained by the reaction of a carboxylic acid compound (5) with thionyl chloride.

Further, in the second production process of the present invention, the amidation can preferably be carried out, for example, by a process in which a carboxylic acid compound of the general formula:

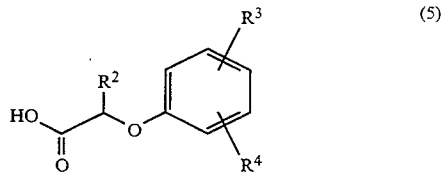

(5)

wherein $R^2$, $R^3$ and $R^4$ are independently a hydrogen atom or a $C_1$–$C_6$ alkyl group, is allowed to react with thionyl chloride, and the resultant reaction mixture is concentrated so as to have a sulfur content of 0.8% or less, preferably 0.5% or less, resulting in an acid chloride compound of the general formula (3), without any distillation of the acid chloride compound as described above, after which the acid chloride compound is then allowed to react with an o-aminophenol hydrochloride salt of the general formula (6).

This case is advantageous as compared with the case where a distilled acid chloride compound is used, because the distillation step can be omitted for convenience and the yield of an acid chloride compound can be prevented from decreasing by distillation.

The reaction of a carboxylic acid compound with thionyl chloride is usually carried out by the same procedures as used when an acid chloride compound is obtained in the first production process of the present invention. To adjust the sulfur content, concentration is carried out, for example, at 65° C. under a reduced pressure of 50 mmHg, preferably 30 mmHg.

When a solvent is used in the reaction of an acid compound with thionyl chloride, the amount of reaction solvent remaining after the concentration is usually reduced to 50% by weight or less, preferably 20% by weight or less, as compared with the amount of reaction solvent before the concentration.

Next, the step of subjecting an o-aminophenol hydrochloride salt of the general formula (6) to amidation condensation with the acid chloride compound of the general formula (3) will hereinafter be explained.

The amount of acid chloride compound to be used is usually 1 to 1.5 times, preferably 1 to 1.35 times, as much as the mole of the o-aminophenol hydrochloride salt of the general formula (3).

The amidation condensation is usually carried out in an inert solvent at 40° to 100° C. Examples of the inert solvent are $C_1$–$C_2$ alkylnitriles such as acetonitrile and propionitrile; aromatic hydrocarbons such as toluene and xylene; and $C_3$–$C_6$ alkylketones such as acetone, 2-butanone, methyl propyl ketone, methyl isopropyl ketone and methyl isobutyl ketone. The amount of inert solvent to be used is usually 3 to 30 times, preferably 3 to 25 times, as much as the weight of the o-aminophenol hydrochloride salt.

The reaction is usually carried out in such a manner that an acid chloride compound is added dropwise to a slurry of the o-aminophenol hydrochloride salt, or both reagents are placed in a reaction vessel at a temperature below 40° C., and heated.

Although the amidation condensation can usually be carried out in air, the reaction is preferably carried out under an atmosphere of an inert gas, such as nitrogen gas, having an oxygen concentration of 5% or less, more preferably 1% or less, to give an aromatic amide compound in a high yield, because oxygen in the atmosphere has an adverse effect on the reaction.

In this reaction, although hydrogen chloride is generated, it is not necessary to use an acid scavenger, and the reaction can proceed smoothly, even if only both reagents are used. When an acid scavenger is used, the reaction can be carried out more easily, and the amount of solvent to be used can be reduced to 3 to 25 times as much as the weight of the o-aminophenol hydrochloride salt.

Examples of inorganic bases which can be used as an acid scavenger are alkali metal carbonates (e.g., sodium carbonate, potassium carbonate) and alkali metal hydrogencarbonates (e.g., sodium hydrogencarbonate, potassium hydrogencarbonate).

The amount of acid scavenger to be used is usually up to about 1.5 times as much as the mole of the o-aminophenol hydrochloride salt when a diacidic base is used as the acid scavenger, and it is up to about 3 times as much as the mole of the o-aminophenol hydrochloride salt when a monoacidic base is used as the acid scavenger.

The reaction mixture after the condensation may be subjected, if necessary, to washing, separation with a separatory funnel or filtration, after which the aromatic amide compound is obtained from the reaction mixture by concentration, and the resultant crude aromatic amide compound may be recrystallized. In the production process of the present invention, however, the reaction mixture after the condensation can be subjected, without any complicated operations as described above, to the subsequent step without any further treatment, or when an acid scavenger is used, the reaction mixture can be subjected, if necessary, to washing, separation with a separatory funnel or filtration, after which it may be subjected either to the subsequent step or to the crystallization step in which a high-quality aromatic amide compound can be obtained as the desired compound from the reaction mixture.

For the crystallization step, the amount of solvent and the solvent composition are conveniently adjusted by the distillation or addition of the reaction solvent, or if necessary, by the addition of water.

The amount of solvent to be used is usually in the range of 3 to 15 times as much as the weight of the raw material o-aminophenol hydrochloride salt. When $C_2$–$C_3$ alkylnitrile solvent such as acetonitrile or propionitrile, or an aromatic hydrocarbon solvent such as toluene or xylene is used in the amidation condensation step, crystallization can be conducted only by adjusting the amount of solvent within the above range.

When acetone is used as a solvent in the condensation step, the solvent composition is adjust to 10–40% water-containing acetone by adding water to the reaction mixture after amidation condensation so as to crystallize the reaction product.

The crystallization is carried out by cooling the reaction mixture usually from a temperature of 40° to 100° C. to a temperature of 5° to 10° C.

The deposited crystals are filtered, washed and dried, which afforded the desired aromatic amide compound as a product having no remaining solvent or water content.

Typical examples of the aromatic amide compound which can be obtained in this process are 2-(2,4-di-t-amylphenoxy)-N-(3,5-dichloro-4-ethyl-2-hydroxyphenyl)butyramide, 2-(2,4-di-t-amylphenoxy)-N-(3,5-dichloro-4-methyl-2-hydroxyphenyl)butyramide, 2-(2,4-di-t-amylphenoxy)-N-(3,5-dichloro-4-ethyl-2-hydroxyphenyl)acetamide, 2-(2,4-di-t-amylphenoxy)-N-(3,5-dichloro-4-methyl-2-hydroxyphenyl)acetamide, 2-(2-t-amyl-4-methylphenoxy)-N-(3,5-dichloro-4-ethyl-2-hydroxyphenyl)butyramide, 2-(2-t-amyl-4-methylphenoxy)-N-(3,5-dichloro-4-methyl-2-hydroxyphenyl)butyramide, 2-(2-t-amyl-4-methylphenoxy)-N-(3,5-dichloro-4-ethyl-2-hydroxyphenyl)acetamide, 2-(2-t-amyl-4-methylphenoxy)-N-(3,5-dichloro-4-methyl-2-hydroxyphenyl)acetamide, 2-(2,4-di-t-amylphenoxy)-N-(3,5-dichloro-4-ethyl-2-hydroxyphenyl)valeramide, 2-(2,4-di-t-amylphenoxy)-N-(3,5-dichloro-4-methyl-2-hydroxyphenyl)valeramide, 2-(2,4-di-t-amylphenoxy)-N-(3,5-dichloro-4-methyl-2-hydroxyphenyl)hexanamide, 2-(2,4-di-t-amylphenoxy)-N-(3,5-dichloro-4-methyl-2-hydroxyphenyl)heptanamide and 2-(2,4-di-t-amylphenoxy)-N-(3,5-dichloro-4-methyl-2-hydroxyphenyl)octanamide.

As described above, the first and second production processes of the present invention can make it possible to readily obtain an aromatic amide compound of the general formula (4) in a high yield, which has a high quality and can therefore be used as a cyan coupler capable of forming excellent images of color photographs.

EXAMPLES

The present invention will be further illustrated by way of the following examples, reference examples and comparative examples, which are not to be construed to limit the scope thereof.

REFERENCE EXAMPLE 1

Synthesis of 2-(2,4-di-t-amylphenoxy)butyric acid (1) Synthesis of ethyl 2-(2,4-di-t-amylphenoxy)butyrate 2,4-Di-t-amylphenol (668.6 g), toluene (1450.9 g) and 95% sodium hydroxide (119.4 g) were placed in a 5-liter flask, and the mixture was dehydrated by azeotropic distillation to have a water content of 400 ppm or less. Then, ethyl 2-bromobutyrate (585 g) was added dropwise at 50° C. for 3 hours. The mixture was kept at 50° C. for 9 hours, and the reaction was completed. To the reaction mixture, concentrated hydrochloric acid (325.3 g) and water (1337.2 g) were added at 40° C. with stirring. The water layer was separated with a separatory funnel, and the oil layer was washed with water (668.6 g). Then, the oil layer was purified by distillation at a temperature of 60° to 250° C. under a reduced pressure of 100 to 3 mmHg with a packed column having the theoretical plate number of 7, which afforded ethyl 2-(2,4-di-t-amylphenoxy)butyrate having a purity of 99% in a yield of 70% on the basis of 2,4-diamylphenol.

(2) Synthesis of 2-(2,4-di-t-amylphenoxy)butyric acid

The above ethyl 2-(2,4-di-t-amylphenoxy)butyrate ester (317.9 g) and 27% aqueous sodium hydroxide (401.4 g) were placed in a 3-liter flask. The mixture was kept at 98° C. for 6 hours, and the hydrolysis reaction was completed. After completion of the reaction, the mixture was adjusted to pH 2 or lower by the addition of 40% aqueous sulfuric acid (349.9 g) and water (250 g), to which toluene (317.9 g) was then added, followed by extraction. The water layer was separated with a separatory funnel, and the toluene layer was washed with water (317.9 g). Then, the toluene layer was concentrated by distillation under ordinary pressure for the recovery of toluene, which afforded a concentrated solution (357.6 g) of the desired carboxylic acid compound in toluene. The analysis revealed that the concentrated solution contained the desired carboxylic acid compound in a yield of 99% yield on the basis of the raw material ester compound.

COMPARATIVE EXAMPLE 1

Production of 2-(2,4-di-t-amylphenoxy)-N-(3,5-dichloro-4-ethyl-2-hydroxyphenyl)butyramide (1) The same concentrated solution (85.5 g) of the carboxylic acid compound as used in Reference Example 1 (2) and N,N-dimethylformamide (0.08 g) were placed in a 1-liter flask, to which thionyl chloride (30.54 g) was added dropwise at 68° C. under an atmosphere of nitrogen gas for 1 hour. The mixture was kept at the same temperature for 4 hours, and the reaction was completed. After completion of the reaction, the remaining thionyl chloride and part of the toluene solution were distilled off at 65° C. under a reduced pressure of 30 mmHg for 3.0 hours, which afforded a concentrated solution (74.51 g) of the acid chloride compound. The analysis revealed that the concentrated solution contained the desired acid chloride compound in a yield of 99% on the basis of the carboxylic acid compound and had a sulfur content of 0.07% based on the weight of the acid chloride compound. (In the following examples, reference examples and comparative examples, all the sulfur contents are also based on the weight of the respective acid chloride compounds.) The above concentrated solution (100 g) of the acid chloride compound was distilled under reduced pressure, which afforded 76.8 g of the purified product (b.p., 139°–140° C./1 mmHg). The distillation recovery of the acid chloride compound was 81.4%.

(2) 2,4-Dichloro-3-ethyl-6-nitrophenol (20 g, 98.4% purity) was dissolved in methanol (300 cc), to which a catalytic amount of Raney nickel was added and into which hydrogen gas was introduced under ordinary pressure until no absorption of hydrogen gas was found. After completion of the reaction, the Raney nickel was removed in air, and the solvent was distilled off. The resultant crude 2,4-dichloro-3-ethyl-6-aminophenol and sodium acetate (16.7 g) were dissolved in glacial acetic acid (500 cc), to which a solution containing acid chloride compound (29.4 g) purified by distillation in acetic acid (70 cc) was added dropwise in 30 minutes. After stirred for 30 minutes, the reaction mixture was poured into ice-water. The precipitate was filtered and dried, after which the precipitate was then recrystallized twice from acetonitrile and dried, which afforded 31.7 g of the desired product (m.p., 145°–146° C., 99.4% purity, 74.3% yield on the basis of the o-nitrophenol compound).

The purity of an amide compound as described herein is determined from the percentage area in the chromatogram of the amide compound by an analysis using a liquid chromatography analyzing apparatus (model LC6A, Shimazu Seisakusho). The analysis conditions are as follows: column, SUMIPACK ODS A212; mobile phase, 0.1% trifluoroacetic acid—10% water-containing acetonitrile; and measurement temperature, 40° C.

The sulfur content was determined by ion chromatography, after the pretreatment of a sample with oxygen flame combustion to convert sulfur into sulfate ions. The determined value was calculated in terms of sulfur and expressed as a value based on the weight of the acid chloride compound.

EXAMPLE 1

Production of 2-(2,4-di-t-amylphenoxy)-N-(3,5-dichloro-4-ethyl-2-hydroxyphenyl)butyramide (1) To a solution containing 2,4-Dichloro-3-ethyl-6-nitrophenol (20 g, 98.4% purity), Raney nickel (0.8 g) and activated carbon (0.2 g) in acetone (320 g), hydrogen gas was introduced at a hydrogen pressure of 4 kg/cm$^2$ at 40° to 45° C. until no absorption of hydrogen gas was found. After completion of the reaction, Raney nickel was removed under an atmosphere of nitrogen gas having an oxygen concentration of 1% or less, which afforded an acetone solution containing 2,4-dichloro-3-ethyl 6-aminophenol.

(2) The concentrated solution (300.6 g) of the carboxylic acid compound in toluene as described in Reference Example 1 (2) and N,N-dimethylformamide (0.25 g) were placed in a 1-liter flask. The mixture was kept at 68° C. under an atmosphere of nitrogen gas, and thionyl chloride (107.34 g) was added dropwise in 1 hour. The mixture was kept at the same temperature with stirring for 4 hours, and the reaction was completed. After completion of the reaction, the mixture was heated to 65° C., and the remaining thionyl chloride and part of the toluene solution were distilled off under a reduced pressure of 30 to 300 mmHg, which afforded a concentrated solution (270 g) of the acid chloride compound in toluene. The analysis revealed that the concentrated solution had a sulfur content of 0.4% and contained the desired 2-(2,4-di-t-amylphenoxy)butyryl chloride in a yield of 99% on the basis of the raw material carboxylic acid compound.

(3) The above acid chloride compound (33.8 g) was added dropwise to a solution of the above 2,4-dichloro-3-ethyl-6-aminophenol in acetone, and the mixture was heated under reflux under an atmosphere of nitrogen gas having an oxygen concentration of 1% or less for 2 hours. Then, acetone (190.8 g) was distilled off under heating, and the reaction was completed. The mixture was cooled to 30° C., and water (43.1 g) was added dropwise after confirmation of the crystal deposition. Further, after the reaction mixture was cooled to 10° C., the crystals were filtered and washed with 25% water containing acetone (64.4 g), and dried, which afforded 39.7 g of the desired amide compound (m.p., 145°–146° C., 99.8% purity, 92.0% yield on the basis of the o-nitrophenol compound).

EXAMPLE 2

Production of
2-(2,4-di-t-amylphenoxy)-N-(3,5-dichloro-4-methyl-2-hydroxyphenyl)butyramide 2,4-Dichloro-3-methyl-6-nitrophenol (20 g, 98.4% purity) was dissolved in acetone (320 g), to which Raney nickel (0.8 g) and activated carbon (0.2 g) were added and into which hydrogen gas was introduced at a hydrogen pressure of 4 kg/cm² until no absorption of hydrogen gas was found. After completion of the reaction, Raney nickel was removed under an atmosphere of nitrogen gas having an oxygen concentration of 1% or less, and the acid chloride compound (35.6 g) as synthesized in Example 1 was added dropwise to the mixture, followed by heating under reflux for 2 hours. Then, acetone (178.3 g) was distilled off under heating, and the reaction was completed. The mixture was cooled to 30° C., and water (35.4 g) was added dropwise after confirmation of the crystal deposition. After cooled to 10° C., the crystals were filtered and washed with 20% water-containing acetone (66.5 g), and dried, which afforded 40.5 g of the desired amide compound (m.p., 150°–151° C., 99.8% purity, 92.0% yield on the basis of the o-nitrophenol compound).

REFERENCE EXAMPLE 2

Synthesis of 2-(2,4-di-t-amylphenoxy)butyric acid (1) Synthesis of ethyl 2-(2,4-di-t-amylphenoxy)butyrate 2,4-Di-t-amylphenol (698 g), toluene (1520 g) and 95% sodium hydroxide (124.6 g) were placed in a 5-liter flask, and the mixture was dehydrated by azeotropic distillation to have a water content of 400 ppm or less. Then, ethyl 2-bromobutyrate (610.7 g) was added dropwise at 50° C. for 3 hours. The mixture was kept at 50° C. for 9 hours, and the reaction was completed. To the reaction mixture, concentrated hydrochloric acid (339.5 g) and water (698 g) were added at 40° C. with stirring. The water layer was separated with a separatory funnel, and the oil layer was washed with water (698 g). Then, the oil layer was concentrated by heating at a temperature of 60° to 250° C. under a reduced pressure of 100 to 10 mmHg for the recovery of toluene and ethyl 2-bromobutyrate, which afforded a concentrated solution (988.2 g) of the ester compound in toluene. The analysis revealed that the concentrated solution contained the desired ester compound in a yield of 91% on the basis of the 2,4-di-t-amylphenol.

(2) Synthesis of 2-(2,4-di-t-amylphenoxy)butyric acid

The above ester-containing concentrated solution (331.3 g) and 27% aqueous sodium hydroxide (401.4 g) were placed in a 3-liter flask. The mixture was kept at 98° C. for 6 hours, and the hydrolysis reaction was completed. After completion of the reaction, the mixture was adjusted to pH 2 or lower by the addition of 40% aqueous sulfuric acid (349.9 g) and water (250 g), and toluene (317.9 g) was added thereto, followed by extraction. The water layer was separated with a separatory funnel, and the toluene layer was washed with water (317.9 g). Then, the toluene layer was concentrated by distillation under ordinary pressure for the recovery of toluene, which afforded a concentrated solution (370.2 g) of the carboxylic acid compound in toluene. The analysis revealed that the concentrated solution contained the desired 2-(2,4-di-t-amylphenoxy)butyric acid in a yield of 99% on the basis of the raw material ester compound.

EXAMPLE 3

Production of
2-(2,4-di-t-amylphenoxy)-N-(3,5-dichloro-4-ethyl-2-hydroxyphenyl)butyramide The concentrated solution (370.2 g) of the carboxylic acid compound in toluene as described in Reference Example 2(2) and N,N-dimethylformamide (0.3 g) were placed in a 2-liter flask, to which thionyl chloride (127.7 g) was added dropwise at 68° C. under an atmosphere of nitrogen gas having an oxygen concentration of 1% or less for 1 hour. The mixture was kept at the same temperature for 4 hours, and the reaction was completed. After completion of the reaction, the remaining thionyl chloride and part of the toluene solution were distilled off at 65° C. under a reduced pressure of 300 to 30 mmHg, which afforded a concentrated solution (333.3 g) of the acid chloride compound in toluene. The analysis revealed that the concentrated solution had a sulfur content of 0.45% and contained the desired 2-(2,4-di-t-amylphenoxy)butyryl chloride in a yield of 99% on the basis of the raw material carboxylic acid compound.

2,4-Dichloro-3-ethyl-6-nitrophenol (20 g, 98.4% purity) was dissolved in acetone (320 g), to which Raney nickel (0.8 g) and activated carbon (0.2 g) were added and into which hydrogen gas was introduced at a hydrogen pressure of 4 kg/cm² until no absorption of hydrogen gas was found. After completion of the reaction, Raney nickel was removed under an atmosphere of nitrogen gas, and the above acid chloride compound (35.1 g) was added dropwise under an atmosphere of nitrogen gas containing an oxygen content of 1% or less, and the reaction mixture was refluxed for 2 hours. Then, acetone (190.8 g) was distilled off under heating, and the reaction was completed. After the reaction mixture was cooled to 30° C., water (43.1 g) was added dropwise after confirmation of the crystal deposition.

The mixture was cooled to 10° C., and the crystals were filtered and washed with 25% water-containing acetone (64.4 g), and dried, which afforded 38 g of the desired amide compound (m.p., 145°–146° C., 99.8% purity, 89.4% yield on the basis of the o-nitrophenol compound).

EXAMPLE 4

Production of 2-(2,4-di-t-amylphenoxy)-N-(3.5-dichloro-4-ethyl-2-hydroxyphenyl)butyramide 2,4-Dichloro-3-ethyl-6-nitrophenol (20 g, 98.4% purity) was dissolved in acetone (320 g), to which Raney nickel (0.8 g) and activated carbon (0.2 g) were added and into which hydrogen gas was introduced at a hydrogen pressure of 4 kg/cm$^2$ until no absorption of hydrogen gas was found. After completion of the reaction, Raney nickel was removed under an atmosphere of nitrogen gas having an oxygen concentration of 0.8%, and the mixture was kept at the same temperature under an atmosphere of nitrogen gas having an oxygen concentration of 0.8% for 24 hours, after which the acid chloride compound (35.1 g) as synthesized in Example 3 was added dropwise under the same conditions, followed by heating under reflux for 2 hours. Then, acetone (190.8 g) was distilled off under heating, and the reaction was completed. After the reaction mixture was cooled to 30° C., water (43.1 g) was added dropwise after confirmation of the crystal deposition. The mixture was cooled to 10° C., and the crystals were filtered and washed with 25% water-containing acetone (64.4 g), and dried, which afforded 38 g of the desired amide compound (m.p., 145°–146° C., 99.8% purity, 89.3% yield on the basis of the o-nitrophenol compound).

REFERENCE EXAMPLE 3

Synthesis of 2-(2,4-di-t-amylphenoxy)acetic acid (1) Synthesis of ethyl 2-(2,4-di-t-amylphenoxy)acetate 2,4-Di-t-amylphenol (668.6 g), toluene (1450.9 g) and 95% sodium hydroxide (119.4 g) were placed in a 5-liter flask, and the mixture was dehydrated by azeotropic distillation to have a water content of 400 ppm or less. Then, ethyl 2-bromoacetate (497.5 g) was added dropwise at 50° C. for 3 hours. The mixture was kept at 50° C. for 9 hours, and the reaction was completed. To the reaction mixture, concentrated hydrochloric acid (325.3 g) and water (1337.2 g) were added at 40° C. with stirring. The water layer was separated with a separatory funnel, and the oil layer was washed with water (668.6 g). Then, the oil layer was purified by distillation at a temperature of 60° to 250° C. under a reduced pressure of 3 to 100 mmHg using a packed column having the theoretical plate number of 7, which afforded ethyl 2-(2,4-di-t-amylphenoxy)acetate having a purity of 98.8% in a yield of 69.5% on the basis of 2,4-di-t-amylphenol.

(2) Synthesis of 2-(2,4-di-t-amylphenoxy)acetic acid

The above ethyl 2-(2,4-di-t-amylphenoxy)acetate (293 g) and 27% aqueous sodium hydroxide (401.4 g) were placed in a 3-liter flask. The mixture was kept at 98° C. for 6 hours, and the hydrolysis reaction was completed. After completion of the reaction, the mixture was adjusted to pH 2 or lower by the addition of 40% aqueous sulfuric acid (349.9 g) and water (250 g), and toluene (289.5 g) was added thereto, followed by extraction. The water layer was separated with a separatory funnel, and the toluene layer was washed with water (289.5 g). Then, the toluene layer was concentrated by distillation under ordinary pressure for the recovery of toluene, which afforded a concentrated solution (357.6 g) of the carboxylic acid compound in toluene. The analysis revealed that the concentrated solution contained the desired carboxylic acid compound in a yield of 99% on the basis of the raw material ester compound.

EXAMPLE 5

Production of 2-(2,4-di-t-amylphenoxy)-N-(3,5-dichloro-4-methyl-2-hydroxyphenyl)acetamide The concentrated solution (307.6 g) of the carboxylic acid compound in toluene as described in Reference Example 3(2) and N,N-dimethylformamide (0.33 g) were placed in a 1-liter flask, and the mixture was kept at 68° C. under an atmosphere of nitrogen gas having an oxygen concentration of 1% or less. Then, thionyl chloride (127.6 g) was added dropwise at 68° C. for 1 hour. The mixture was kept at the same temperature with stirring for 4 hours, and the reaction was completed. After completion of the reaction, the remaining thionyl chloride and part of the toluene solution were distilled off under heating to 65° C. under a reduced pressure of 300 to 30 mmHg, which afforded a concentrated solution (287.8 g) of the acid chloride compound in toluene. The analysis revealed that the concentrated solution had a sulfur content of 0.4% and contained the desired 2-(2,4-di-t-amylphenoxy)acetyl chloride in a yield of 99% on the basis of the raw material carboxylic acid compound.

2,4-Dichloro-3-methyl-6-nitrophenol (20 g, 98.6% purity) was dissolved in acetone (320 g), to which Raney nickel (0.8 g) and activated carbon (0.2 g) were added and into which hydrogen gas was introduced at a hydrogen pressure of 4 kg/cm$^2$ at a temperature of 40° to 45° C. until no absorption of hydrogen gas was found. After completion of the reaction, Raney nickel was removed under an atmosphere of nitrogen gas having an oxygen concentration of 1% or less, and the above acid chloride compound (31.9 g) was added dropwise, followed by heating under reflux for 2 hours. Then, acetone (194.8 g) was distilled off under heating, and the reaction was completed. After the reaction mixture was cooled to 30° C., water (41.8 g) was added dropwise after confirmation of the crystal deposition. The mixture was cooled to 10° C., and the crystals were filtered and washed with 25% water-containing acetone (62.0 g), and dried, which afforded 39.6 g of the desired amide compound (m.p., 151°–152° C., 99.7% purity, 95.3% yield on the basis of the o-nitrophenol compound).

COMPARATIVE EXAMPLE 2

In this comparative example, an acid chloride compound having a sulfur content of 0.8% was used in the amidation condensation.

The concentrated solution (57 g) of 2-(2,4-di-t-amylphenoxy)butyric acid as described in Reference Example 1 (2) and N,N-dimethylformamide (0.05 g) were placed in a 1-liter flask, and the mixture was kept at 68° C. under an atmosphere of nitrogen gas having an oxygen concentration of 1% or less. Then, thionyl chloride (20.36 g) was added dropwise at 68° C. for 1 hour. The mixture was kept at the same temperature with stirring for 4 hours, and the reaction was completed. After completion of the reaction, the remaining thionyl chloride and part of the toluene solution were distilled off under heating to 65° C. under a reduced pressure of 300 to 50 mmHg, which afforded a concentrated solution (51.98 g) of the acid chloride compound. The analysis revealed that the concentrated solution had a sulfur content of 0.8% and contained the desired acid chloride compound in a yield of 99% on the basis of the raw material carboxylic acid compound.

The same procedures were conducted in the same manner as described in Example 1, except that the above acid chloride compound having a sulfur content of 0.8% was used. As the result, 33.6 g of 2-(2,4-di-t-amylphenoxy)-N-(3,5-dichloro-4-ethyl-2-hydroxyphenyl)butyramide was obtained (m.p., 145°-146° C., 99.5% purity, 77.6% yield on the basis of the o-nitrophenol compound).

COMPARATIVE EXAMPLE 3

In this comparative example, condensation amidation was carried out under an atmosphere of nitrogen gas having an oxygen concentration of 5%.

2,4-Dichloro-3-ethyl-6-nitrophenol (20 g) was dissolved in acetone (320 g), to which Raney nickel (0.8 g) and activated carbon (0.2 g) were added and into which hydrogen gas was introduced at a hydrogen pressure of 4 kg/cm$^2$ until no absorption of hydrogen gas was found. After completion of the reaction, Raney nickel was removed, and the acid chloride compound (35.1 g) as synthesized in Example 2 was added dropwise under an atmosphere of nitrogen gas having an oxygen concentration of 5%, and refluxed for 2 hours. Then, acetone (190.8 g) was distilled off under heating, and the reaction was completed. After the reaction mixture was cooled to 30° C., water (43.1 g) was added dropwise after confirmation of the crystal deposition. The mixture was cooled to 10° C., and the crystals were filtered and washed with 25% water-containing acetone (64.4 g), and dried, which afforded 33.7 g of the desired amide compound (m.p., 145°-146° C., 99.6% purity, 77.9% yield on the basis of the o-nitrophenol compound).

EXAMPLE 6

Production of 2-(2,4-di-t-amylphenoxy)-N-(3,5-dichloro-4-ethyl-2-hydroxyphenyl)butyramide 2,4-Dichloro-3-ethyl-6-nitrophenol (20 g, 98.4% purity) was dissolved in xylene (80 g), to which Raney nickel (0.8 g) and activated carbon (0.2 g) were added and into which hydrogen gas was introduced at a hydrogen pressure of 4 kg/cm$^2$ until no absorption of hydrogen gas was found. After completion of the reaction, Raney nickel was removed under an atmosphere of nitrogen gas having an oxygen concentration of 1% or less, and sodium hydrogencarbonate (8.4 g) was added. To this mixture, the acid chloride compound (33.8 g) as synthesized in Example 1 was added dropwise under an atmosphere of nitrogen gas having an oxygen concentration of 1% or less, followed by heating under reflux for 2 hours. Then, the undissolved matter was filtered, and the xylene solution was cooled to 5° C. The deposited crystals were filtered and washed with xylene (20 g), and dried, which afforded 35.9 g of the desired amide compound (m.p., 145°-146° C., 99.7% purity, 84.5% yield on the basis of the o-nitrophenol compound).

EXAMPLE 7

Production of 2-(2,4-di-t-amylphenoxy)-N-(3,5-dichloro-4-ethyl-2-hydroxyphenyl)butyramide 2,4-Dichloro-3-ethyl-6-nitrophenol (20 g, 98.4% purity) was dissolved in acetone (100 g), to which Raney nickel (0.8 g) and activated carbon (0.2 g) were added and into which hydrogen gas was introduced at a hydrogen pressure of 4 kg/cm$^2$ until no absorption of hydrogen gas was found. After completion of the reaction, Raney nickel was removed under an atmosphere of nitrogen gas having an oxygen concentration of 1% or less, and sodium hydrogencarbonate (7.0 g) was added. To this mixture, the acid chloride compound (33.8 g) as synthesized in Example 1 was added dropwise under an atmosphere of nitrogen gas having an oxygen concentration of 1% or less, followed by heating under reflux for 2 hours. Then, the undissolved matter in the reaction mixture was filtered and washed with a small amount of acetone. After the addition of water (4.3 g) and acetone (24.2 g), the mixture was cooled to 30° C. After the deposition of crystals, water (38.8 g) was added dropwise, and the mixture was further cooled to 10° C. The deposited crystals were filtered and washed with 25% water-containing acetone (64.4 g), and dried, which afforded 39.7 g of the desired amide compound (m.p., 145°-146° C., 99.8% purity, 93.5% yield on the basis of the o-nitrophenol compound).

EXAMPLE 8

Production of 2-(2,4-di-t-amylphenoxy)-N-(3,5-dichloro-4-ethyl-2-hydroxyphenyl)butyramide The reaction was carried out under the same conditions as described in Example 7, except that sodium carbonate (8.8 g) was used in place of sodium hydrogencarbonate, which afforded 35.1 g of the desired amide compound (m.p., 145°-146° C., 99.7% purity, 82.5% yield on the basis of the o-nitrophenol compound).

REFERENCE EXAMPLE 4

Synthesis of 2-(2,4-di-t-amylphenoxy)butyric acid (1) Synthesis of ethyl 2-(2,4-di-t-amylphenoxy)butyrate 2,4-Di-t-amylphenol (668.6 g), toluene (1450.9 g) and 95% sodium hydroxide (119.4 g) were placed in a 5-liter flask, and the mixture was dehydrated by azeotropic distillation to have a water content of 400 ppm or less. Then, ethyl 2-bromobutyrate (585 g) was added dropwise at 50° C. for 3 hours. The mixture was kept at the same temperature for 9 hours, and the reaction was completed. To the reaction mixture, concentrated hydrochloric acid (325.3 g) and water (1337.2 g) were added at 40° C. with stirring. The water layer was separated with a separatory funnel, and the oil layer was washed with water (668.6 g). Then, the oil layer was purified by distillation at a temperature of 60° to 250° C. under a reduced pressure of 100 to 3 mmHg with a packed column having the theoretical plate number of 7, which afforded ethyl 2-(2,4-di-t-amylphenoxy)butyrate having a purity of 99% in a yield of 70% on the basis of 2,4-diamylphenol.

(2) Synthesis of 2-(2,4-di-t-amylphenoxy)butyric acid

The above ethyl 2-(2,4-di-t-amylphenoxy)butyrate (317.9 g) and 27% aqueous sodium hydroxide (401.4 g) were placed in a 3-liter flask. The mixture was kept at 98° C. for 6 hours, and the hydrolysis reaction was completed. After completion of the reaction, the mixture was adjusted to pH 2 or lower by the addition of 40% aqueous sulfuric acid (349.9 g) and water (250 g), and toluene (317.9 g) was added thereto, followed by extraction. The water layer was separated with a separatory funnel, and the toluene layer was washed with water (317.9 g). Then, the toluene layer was concentrated by distillation under ordinary pressure for the removal of toluene, which afforded a concentrated solution (357.6 g) of the carboxylic acid compound in toluene. The analysis revealed that the concentrated solution contained the desired carboxylic acid compound in a yield of 99% on the basis of the raw material ester compound.

EXAMPLE 9

Production of 2-(2,4-di-t-amylphenoxy)-N-(3,5-dichloro-4-ethyl-2-hydroxyphenyl)butyramide The concentrated solution (85.5 g) having the same composition as the concentrated solution of the carboxylic acid compound as obtained in Reference Example 4(2) and N,N-dimethylformamide (0.08 g) were placed in a 1-liter flask, to which thionyl chloride (30.54 g) was added dropwise at 68° C. under an atmosphere of nitrogen gas for 1 hour. The mixture was kept at the same temperature for 4 hours, and the reaction was completed. After completion of the reaction, the remaining thionyl chloride and part of the toluene solution were distilled off at 65° C. under a reduced pressure of 30 mmHg for 3.0 hours, which afforded a concentrated solution (74.51 g) of the acid chloride compound in toluene. The analysis revealed that the concentrated solution contained the acid chloride compound in a yield of 99% on the basis of the carboxylic acid compound and had a sulfur content of 0.07% based on the weight of the acid chloride compound.

The acid chloride compound (30.8 g), 6-amino-2,4-dichloro-3-ethylphenol hydrochloride (20.7 g, 97.5% content) and acetonitrile (207 g) were placed in a flask, and the mixture was heated under reflux under an atmosphere of nitrogen gas having an oxygen concentration of 1% or less for 3 hours. After completion of the reaction, the reaction mixture was cooled to 10° C. and kept at the same temperature for 1 hour, which resulted in a crystallization of the amide compound. The deposited crystals were filtered and washed with acetonitrile, and dried, which afforded 39.9 g of the desired product (m.p., 145°-146° C., 99.8% purity, 94.1% yield in the amidation step).

EXAMPLE 10

Production of 2-(2,4-di-t-amylphenoxy)-N-(3,5-dichloro-4-ethyl-2-hydroxyphenyl)butyramide The concentrated solution (85.5 g) having the same composition as the concentrated solution of the carboxylic acid compound as obtained in Reference Example 4(2) and N,N-dimethylformamide (0.08 g) were placed in a 1-liter flask, to which thionyl chloride (30.54 g) was added dropwise at 68° C. under an atmosphere of nitrogen gas for 1 hour. The mixture was kept at the same temperature for 4 hours, and the reaction was completed. After the completion of the reaction, the remaining thionyl chloride and part of the toluene solution were distilled off at 65° C. under a reduced pressure of 30 mmHg for 2 hours, which afforded a concentrated solution (75.26 g) of the acid chloride compound in toluene. The analysis revealed that the concentrated solution contained the acid chloride compound in a yield of 99% on the basis of the carboxylic acid compound and had a sulfur content of 0.13% on the basis of the acid chloride compound.

The reaction was carried out in the same manner as described in Example 9, except that the acid chloride compound (31.1 g, 0.13% sulfur content) was used, which afforded the desired product (m.p., 145°-146° C., 99.7% purity, 94.6% yield in the amidation step).

EXAMPLE 11

Production of 2-(2,4-di-t-amylphenoxy)-N-(3,5-dichloro-4-ethyl-2-hydroxyphenyl)butyramide The concentrated solution (300.6 g) of the carboxylic acid compound in toluene as obtained in Reference Example 1 (2) and N,N-dimethylformamide (0.25 g) were placed in a 1-liter flask, to which thionyl chloride (107.34 g) was added dropwise at 68° C. under an atmosphere of nitrogen gas for 1 hour. The mixture was kept at the same temperature with stirring for 4 hours, and the reaction was completed. After the completion of the reaction, the mixture was heated to 65° C., and the remaining thionyl chloride and part of the toluene solution were distilled off under a reduced pressure of 30 to 300 mmHg, which afforded a concentrated solution (270 g) of the acid chloride compound in toluene. The analysis revealed that the concentrated solution had a sulfur content of 0.4% and contained the desired acid chloride compound in a yield of 99% on the basis of the raw material carboxylic acid compound.

The reaction was carried out in the same manner as described in Example 1, except that the acid chloride compound (33.8 g, 0.40% sulfur content) was used, which afforded the desired product (m.p., 145°-146° C., 99.6% purity, 93.5% yield in the amidation step).

EXAMPLE 12

Production of 2-(2,4-di-t-amylphenoxy)-N-(3,5-dichloro-4-ethyl-2-hydroxyphenyl)butyramide (1) The concentrated solution (300.6 g) having the same composition as the concentrated solution of 2-(2,4-di-t-amylphenoxy)butyric acid in toluene as obtained in Reference Example 1 (2) and N,N-dimethylformamide (0.25 g) were placed in a 1-liter flask, to which thionyl chloride (107.34 g) was added dropwise at 68° C. under an atmosphere of nitrogen gas for 1 hour. The mixture was kept at the same temperature with stirring for 4 hours, and the reaction was completed. After completion of the reaction, the mixture was heated to 65° C., and the remaining thionyl chloride and part of the toluene solution were distilled off under a reduced pressure of 30 to 300 mmHg, which afforded a concentrated solution (270 g) of the acid chloride compound in toluene. The analysis revealed that the concentrated solution had a sulfur content of 0.4% and contained the desired acid chloride compound in a yield of 99% on the basis of the raw material carboxylic acid compound.

(2) The concentrated solution (100 g) of the acid chloride compound was distilled under reduced pressure, which afforded 76.8 g of the purified product (b.p., 139°–140° C./1 mmHg). The distillation recovery of the acid chloride compound was 81.4% and the sulfur content was 0.01% or less.

(3) 2,4-Dichloro-3-ethyl-6-nitrophenol (20 g, 98.4% purity) was dissolved in methanol (80 g), to which Raney nickel (0.8 g) and activated carbon (0.2 g) were added and into which hydrogen gas was introduced at a hydrogen pressure of 4 kg/cm² at 40° to 45° C. until no absorption of hydrogen gas was found. After completion of the reaction, Raney nickel was removed in air, and hydrochloric acid (17.7 g) was added dropwise, and the reaction mixture was cooled to 20° C., which resulted in a deposition of crystals. The deposited crystals were washed with acetone (28 g) and dried, which afforded 16.2 g of 2,4-dichloro-3-ethyl-6-aminophenol hydrochloride. To this hydrochloride salt, the above distillation-purified acid chloride compound (23.4 g) was added in air, and the mixture was heated under reflux in acetonitrile (162 g) for 2 hours. After completion of the reaction, the reaction mixture was cooled to 10° C., and the deposited crystals were filtered, washed with acetonitrile (16 g) and dried, which afforded 30.1 g of the desired amide compound (m.p., 145°–146° C., 98.9% purity). These crystals were recrystallized from acetonitrile (150 g), and 28.2 g of crystals having a purity of 99.3% were obtained (82.2% yield in the amidation step).

EXAMPLE 13

In this example, an acid chloride compound having a sulfur content of 0.8% was used in the amidation condensation.

The concentrated solution (57 g) of 2-(2,4-di-t-amylphenoxy)butyric acid as described in Reference Example 4(2) and N,N-dimethylformamide (0.05 g) were placed in a 1-liter flask, to which thionyl chloride (20.36 g) was added dropwise at 68° C. under an atmosphere of nitrogen gas for 1 hour. The mixture was kept at the same temperature with stirring for 4 hours, and the reaction was completed. After completion of the reaction, the mixture was heated to 65° C., and the remaining thionyl chloride and part of the toluene solution were distilled off under a reduced pressure of 300 to 50 mmHg, which afforded a concentrated solution (51.98 g) of the acid chloride compound in toluene. The analysis revealed that the concentrated solution had a sulfur content of 0.8% and contained the desired acid chloride compound in a yield of 99% on the basis of the raw material carboxylic acid compound.

The same procedures were conducted as described in Example 9, except that the acid chloride compound having a sulfur content of 0.8% was used. As the result, 33.6 g of 2-(2,4-di-t-amylphenoxy)-N-(3,5-dichloro-4-ethyl-2-hydroxyphenyl)butyramide was obtained (m.p., 145°–146° C., 99.5% purity, 79.0% yield in the amidation step).

EXAMPLE 14

In this example, the reaction was carried out under an atmosphere having an oxygen concentration of 5%.

The same procedures were conducted as described in Example 9, except that the reaction was carried out under an atmosphere of nitrogen gas having an oxygen concentration of 5%. As the result, 37.4 g of 2-(2,4-di-t-amylphenoxy)-N-(3,5-dichloro-4-ethyl-2-hydroxyphenyl)butyramide was obtained (m.p., 145°–146° C., 99.6% purity, 88.0% yield in the amidation step).

EXAMPLE 15

Production of 2-(2,4-di-t-amylphenoxy)-N-(3,5-dichloro-4-ethyl-2-hydroxyphenyl)butyramide 6-Amino-2,4-dichloro-3-ethylphenol hydrochloride (20.7 g, 97.5% content), acetone (140 g) and sodium hydrogencarbonate (14.0 g) were placed in a flask, to which the acid chloride compound (33.8 g, 0.40% sulfur content) as obtained in Example 11 was added dropwise under an atmosphere of nitrogen gas having an oxygen concentration of 1% or less, followed by heating under reflux for 2 hours. After completion of the reaction, the undissolved matter in the reaction mixture was filtered off and washed with a small amount of acetone. To the combined filtrate and the washing liquid, water (4.3 g) and acetone (24.2 g) were added, after which the mixture was cooled to 30° C. After confirmation of the crystal deposition, water (38.8 g) was further added dropwise to this mixture. The mixture was further cooled to 10° C., and the deposited crystals were filtered and washed with 25% water-containing acetone (64.4 g), and dried, which afforded 38.1 g of the desired amide compound (m.p., 145°–146° C., 99.7% purity, 89.6% yield in the amidation step).

EXAMPLE 16

Production of 2-(2,4-di-t-amylphenoxy)-N-(3,5-dichloro-4-ethyl-2-hydroxyphenyl)butyramide The same procedures were conducted as described in Example 12, except that sodium carbonate (17.6 g) was used as an acid scavenger in place of sodium hydrogencarbonate. As the result, 34.1 g of the desired amide compound was obtained (m.p., 145°–146° C., 99.7% purity, 80.2% yield in the amidation step).

What is claimed is:

1. A process for producing an aromatic amide compound of the general formula:

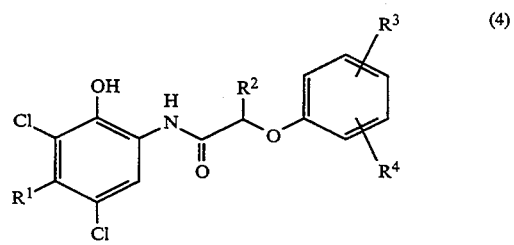

wherein $R^1$ is a $C_1$–$C_4$ alkyl group, and $R^2$, $R^3$ and $R^4$ are independently a hydrogen atom or a $C_1$–$C_6$ alkyl group, said process comprising the steps of:
(a) subjecting an o-nitrophenol compound of the general formula:

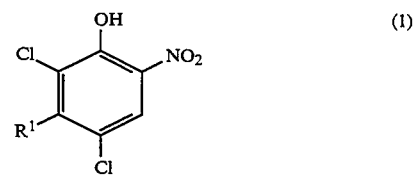

wherein R¹ is as defined above, to catalytic reduction in acetone or an aromatic hydrocarbon solvent under the presence of a nickel catalyst to give an o-aminophenol compound of the general formula:

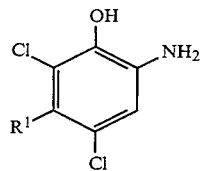
(2)

wherein R¹ is as defined above; and (b) subjecting the reaction mixture containing the o-aminophenol compound obtained in the step (a) to condensation with an acid chloride compound having a sulfur content of 0.5% or less, based on the weight of the acid chloride compound, of the general formula:

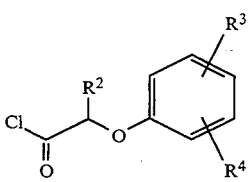
(3)

wherein R², R³ and R⁴ are each as defined above under an atmosphere of an inert gas having an oxygen concentration of 1% or less.

2. A process for producing an aromatic amide compound of the general formula:

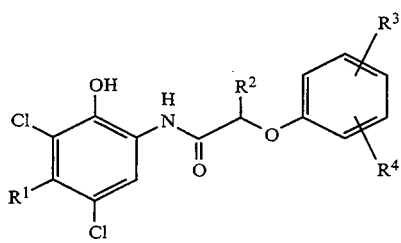
(4)

where in R¹ is a $C_1$–$C_4$ alkyl group, and R², R³ and R⁴ are independently a hydrogen atom or a $C_1$–$C_6$ alkyl group, said process comprising the steps of:

(a) allowing a carboxylic acid compound of the general formula:

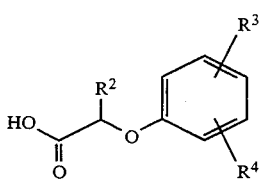
(5)

wherein R², R³ and R⁴ are independently a hydrogen atom or a $C_1$–$C_6$ alkyl group, to react with thionyl chloride, and concentrating the reaction mixture to give an acid chloride compound having a sulfur content of 0.5% or less, based on the weight of the acid chloride compound, of the general formula:

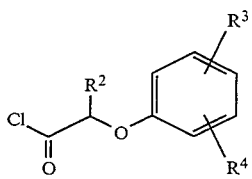
(3)

wherein R², R³ and R⁴ are each as defined above;

(b) subjecting an o-nitrophenol compound of the general formula:

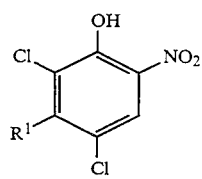
(1)

wherein R¹ is as defined above, to catalytic reduction in acetone or an aromatic hydrocarbon solvent under the presence of a nickel catalyst to give an o-aminophenol compound of the general formula:

(2)

wherein R¹ is as defined above; and (c) subjecting the reaction mixture containing the o-aminophenol compound obtained in the step (b) to condensation with the acid chloride compound obtained in the step (a) under an atmosphere of an inert gas having an oxygen concentration of 1% or less.

3. A process according to claim 1 or 2, wherein the solvent used in the catalytic reduction and the condensation is aromatic hydrocarbon solvent, and after completion of the condensation, the aromatic amide compound of the general formula (4) is crystallized from the reaction mixture.

4. A process according to claim 1 or 2, wherein the solvent used in the catalytic reduction and the condensation is acetone, and after completion of the condensation, water is added to the reaction mixture so that the aromatic amide compound of the general formula (4) is crystallized therefrom.

5. A process according to claim 1, wherein the catalytic reduction is carried out under the coexistence of activated carbon.

6. A process according to claim 1, wherein the condensation is carried out under the presence of an acid scavenger.

7. A process according to claim 6, wherein the acid scavenger is sodium hydrogencarbonate.

8. A process for producing an aromatic amide compound of the general formula:

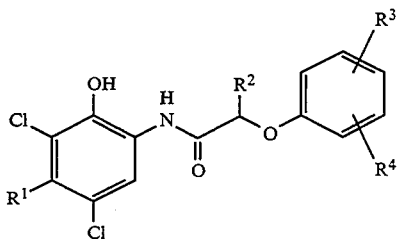 (4)

wherein $R^1$ is a $C_1$-$C_4$ alkyl group, and $R^2$, $R^3$ and $R^4$ are independently a hydrogen atom or a $C_1$-$C_6$ alkyl group, said process comprising the step of:

subjecting an o-aminophenol hydrochloride salt of the general formula:

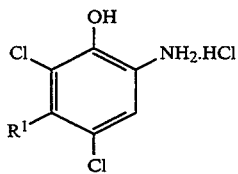 (6)

wherein $R^1$ is as defined above, to condensation with an acid chloride compound having a sulfur content of 0.8% or less, based on the weight of the acid chloride compound, of the general formula:

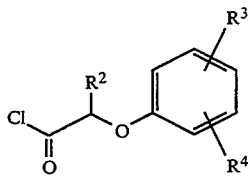 (3)

wherein $R^2$, $R^3$ and $R^4$ are each as defined above, in an inert solvent which is selected from $C_2$-$C_3$ alkylnitrile and acetone, under an atmosphere of an inert gas having an oxygen concentration of 5% or less.

9. A process according to claim 8, wherein a carboxylic acid compound of the general formula:

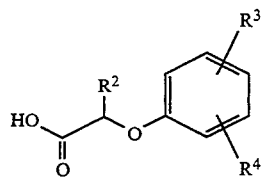 (5)

wherein $R^2$, $R^3$ and $R^4$ are each as defined above, is allowed to react with thionyl chloride and the resultant reaction mixture is concentrated, after which the acid chloride compound having a sulfur content of 0.8% or less, based on the weight of the acid chloride compound, of the general formula (3) is used.

10. A process according to claim 8 or 9, wherein the acid chloride compound of the general formula (3) has a sulfur content of 0.5% or less, based on the weight of the acid chloride compound.

11. A process according to claim 8, wherein the condensation is carried out under an atmosphere of an inert gas having an oxygen concentration of 1% or less.

12. A process according to claim 8, wherein the solvent used in the condensation is $C_2$-$C_3$ alkylnitrile, and after completion of the condensation, the aromatic amide compound of the general formula (4) is crystallized from the reaction mixture.

13. A process according to claim 8, wherein the solvent used in the condensation is acetone, and after completion of the condensation, water is added to the reaction mixture so that the aromatic amide compound of the general formula (4), is crystallized therefrom.

14. A process according to claim 8, wherein the condensation is carried out under the presence of inorganic bases.

* * * * *